(12) United States Patent
Borneman et al.

(10) Patent No.: US 6,204,008 B1
(45) Date of Patent: *Mar. 20, 2001

(54) BIOPROCESS FOR PRODUCTION OF DIPEPTIDE BASED COMPOUNDS

(75) Inventors: W. Scott Borneman, San Carlos, CA (US); Anil Goyal, New Brunswick, NJ (US); Michael J. Conder, McGaheysville; Victor A. Vinci, Charlottesville, both of VA (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/748,073

(22) Filed: Nov. 12, 1996

Related U.S. Application Data

(63) Continuation of application No. 08/419,787, filed on Apr. 11, 1995, now abandoned.

(51) Int. Cl.[7] .................................................... C12P 21/06
(52) U.S. Cl. ........................ 435/69.1; 435/219; 435/220; 435/252.33
(58) Field of Search ................................. 435/69.1, 68.1, 435/219, 221, 252.33

(56) References Cited

U.S. PATENT DOCUMENTS

| | | |
|---|---|---|
| 4,374,829 | 2/1983 | Harris ................................... 424/177 |
| 4,555,502 | 11/1985 | Patchett ................................. 514/19 |
| 4,888,284 | 12/1989 | Konings ............................... 435/183 |
| 5,089,406 | 2/1992 | Williams ........................... 435/172.3 |
| 5,521,081 * | 5/1996 | Inaoka et al. ......................... 435/212 |

FOREIGN PATENT DOCUMENTS

| | | |
|---|---|---|
| 0 036 258 | 9/1981 | (EP) . |
| 0 165 492 B1 | 12/1985 | (EP) . |
| 0 528 686 A2 | 2/1993 | (EP) . |
| 2068971B | 6/1983 | (GB) . |
| 9206211 * | 4/1992 | (WO) . |
| WO9416082 | 12/1994 | (WO) . |

OTHER PUBLICATIONS

Yamamoto, N. et al. "Antihypertensive effect of the peptides derived from casein by an extracellular proteinase from *Lactobacillus helveticus* CP790." Journal of Diary Science, vol. 44, No. 4 (Apr. 1994), pp. 917–922.*

Hong, J.C. et al. (1987) "Characterization and sequence analysis of a developmentally regulated putative cell wall protein gene isolated from soybean" *J. Biol. Chem* 262(17):8367–8376.*

Kreil, G. (1990) "Processing of precursors by dipeptidylaminopeptidases: a case of molecular ticketing" *Trends in Biochem. Sci.* 15:23–26.*

Nagamori, Y. et al. (1991) "Enzymatic properties of dipeptidyl carboxypeptidase from *Bacillus pumilus*" *Agric. Biol. Chem.* 55(7):1695–1699.*

Maina, C.V. et al. (1988) "An *Escherichia coli* vector to express and purify foreign proteins by fusion to and separation from maltose–binding protein" Gene, vol. 74, pp. 365–373.*

Pohlner, J. et al. "Sequence–Specific Cleavage of Protein Fusions Using a Recombinant Neisseria Type 2 IgA Protease" Bio/Technology, vol. 10, 1992 p799–804.

Lloyd R. et al. "Characterization of X–prolyl dipeptidyl aminopeptidase from *lactococcus lactis* subsp. *lactis*", J. Gen. Micro. (1991) vol. 137, pp 49–55.

Khalid et al. "Purification and Partial Characterizationof a Prolyl–Dipeptidyl Aminopeptidase from *Lactobacillus helveticus* CNRZ32", Applied and Environment Microbiolocy 1990, p 381–388.

Hofer R, "Construction and stability of a sixfold repeated artificial gene", J. Biochem, 167, (1987) p 307–313.

Fieschko, "III. Amino Acids", Biotechnology, vol. 7b (1988) pp 235–238 and 253.

Doel et al., "The expression in *E. coli* of synthetic repeating polymeric genes coding for poly (L–aspartyl–L–phenylalanine", Nucleic Acids Research, vol. 8, No. 20, (1980) p 4575–4592.

Creel et al. "Genetically Directed Syntheses of New Polymeric Materials. Efficient Expression of a Monodisperse Copolypeptide Containing Fourteen Tandemly Repeated–(AlaGly)4ProGluGly–Elements", Macromolecules (1991) vol. 24, pp. 1213–1214.

Barrett et al. "Oligopeptidases, and the Emergence of the Prolyl Oligopeptidase Family", Biol. Chem., vol. 373 (1992) pp353–360.

Hong, et al. "Characterization of a Proline–rich Cell Wall Protein Gene Family of Sobyean", J. of Biol. Chem., vol. 265, No. 5 (1990), pp. 2470–2475.

Gmachl et al. "Dermal glands of *Xenopus laevis* contain a polypeptide with a highly repetitive amino acid sequence", FEB, vol. 260, No. 1, (1990) pp 145–148.

Yoshimoto et al., "Post Proline Dipeptidylaminopeptidase EC–3.4.14.1. Dipeptidylamino Peptidase IV from Lamb Kidney, Purification and Some Enzymatic Properties," Biochim Biophys Acta, vol. 485, No. 2, pp. 391–401, 1977.*

Kato et al., "Successive Cleavage of N–Terminal $Arg^1–Pro^2$ and $Lys^3–Pro^4$ from Substance P . . . ," Biochim Biophys Acta vol. 525, No. 2, pp. 417–422, 1978.*

* cited by examiner

Primary Examiner—Nashaat T. Nashed
Assistant Examiner—Christian L Fronda
(74) Attorney, Agent, or Firm—J. Mark Hand; Jack L. Tribble

(57) ABSTRACT

Bioprocesses are disclosed for the production of compounds which can be produced from a dipeptide intermediate. The process comprises production of a recombinant polypeptide which contains the dipeptide intermediate. The dipeptide intermediate is further processed to ultimately provide the finished product.

13 Claims, No Drawings

BIOPROCESS FOR PRODUCTION OF DIPEPTIDE BASED COMPOUNDS

This application is a continuation of application Ser. No. 08/419,787 filed on Apr. 11, 1995, now abandoned.

BACKGROUND OF THE INVENTION

The large scale production of compounds which are based, at least in part, on a dipeptide intermediate requires the ready availability of large quantities of the dipeptide intermediate at low cost. Dipeptides of virtually any amino acids may be synthetically prepared for this use, however, synthesis of the dipeptide can be time consuming and costly which reduces the efficiency of product production and increases production costs. These disadvantages are particularly important to very large scale production of the dipeptide intermediate-based compounds.

SUMMARY OF THE DISCLOSURE

A process for the production of dipeptide intermediate compounds is disclosed. These dipeptide intermediate compounds are produced by recombinant DNA techniques and are produced from a synthetic DNA sequence or from a naturally-occurring DNA sequence, both of which encode a protein or peptide having a specific repeating dipeptide sequence. The dipeptide intermediates are enzymatically liberated from the larger protein or peptide and further processed to provide the finished compound.

DETAILED DESCRIPTION OF THE INVENTION

The present invention is drawn to a process for the preparation of dipeptide intermediate compounds. These intermediate compounds can be further processed to produce the finished compound. The dipeptide intermediates are produced in recombinant host cells through the expression of a recombinant DNA molecule, which encodes at least one dipeptide intermediate. The recombinant DNA molecule can be either a synthetic DNA molecule or a naturally occurring DNA sequence. The DNA encoding the dipeptide is cloned into an expression vector for expression in a recombinant host cell. Following expression in the recombinant host the dipeptide is purified for further processing. It may be necessary to separate the dipeptide from a larger polypeptide before it can be purified. A larger polypeptide containing the dipeptide intermediate may be comprised of multiple repeats of the dipeptide sequence, or the dipeptide may be present in one or more copies as part of a larger protein containing amino acid sequences that are not the dipeptide sequence. The repeats of the dipeptide sequence may be separated into individual dipeptides by enzymatic or chemical cleavage. The individual dipeptides may then be purified for further processing.

The recombinant host cells used to produce the dipeptide can be any host cell that is capable of expressing recombinant DNA molecules. It is readily apparent to those skilled in the art that virtually any recombinant host is suitable for use in the process of the present invention. The preferred host cells include, but are not limited to, bacteria and fungal host cells including yeast. Bacterial and fungal host cells which are suitable for use in the present invention and are commercially available include, but are not limited to, *Sacccharomyces cerevisiae, Pichia pastoris, Escherichia coli, Aspergillus niger, Streptomyces lividans*, and *Bacillus subtilis*.

It is also readily apparent to those skilled in the art that the expression vector for expressing the DNA encoding the dipeptide can be virtually any expression vector suitable for use in the chosen host cell. The preferred vectors include, but are not limited to, those suitable for use in bacteria and fungal cells including yeast. Bacterial and fungal expression vectors which are suitable for use in the present inventions and are commercially available include, but are not limited to those listed herein.

The separation of the dipeptide from the remaining non-dipeptide sequences, or the separation of individual dipeptides from dipeptide repeats is performed enzymatically using an enzyme which cleaves the polypeptide in the appropriate position without destroying the dipeptide intermediate. Enzymes suitable for use in the process of the present invention can be those which are commercially available or those produced by an organism which possesses the appropriate enzymatic activity. The selection of an appropriate enzyme will depend upon the particular dipeptide sequence being expressed.

The dipeptide may be purified either before or after it is separated from the remainder of the polypeptide or from repeats of the dipeptide. Standard chromatographic techniques are suitable for use in the process of the present invention to purify the individual dipeptides or the dipeptide-containing polypeptide. Such standard chromatographic techniques include, but are not limited to salt fractionation, ion exchange chromatography, size exclusion chromatography, hydroxylapatite adsorption chromatography, and hydrophobic interaction chromatography.

The cloned DNA obtained through the methods described herein may be recombinantly expressed by molecular cloning into an expression vector containing a suitable promoter and other appropriate transcription regulatory elements, and transferred into prokaryotic or eukaryotic host cells to produce recombinant peptide. Techniques for such manipulations are fully described in Sambrook, J., et al., supra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, plant cells, insect cells, fungal cells and animal cells.

Specifically designed vectors allow the shuttling of DNA between hosts such as bacteria-yeast or bacteria-animal cells or bacteria-fungal cells or bacteria-invertebrate cells. An appropriately constructed expression vector should contain; an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant peptide in mammalian cells. Commercially available mammalian expression vectors which may be suitable for recombinant peptide expression include, but are not limited to, pcDNA3 (Invitrogen), pMClneo (Stratagene), pXTI (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and λZD35 (ATCC 37565).

A variety of bacterial expression vectors may be used to express recombinant peptide in bacterial cells. Commercially available bacterial expression vectors which may be suitable for recombinant peptide expression include, but are not limited to, pET11a (Novagen), lambda gt11 (Invitrogen), pcDNAII (Invitrogen), pKK223-3 (Pharmacia).

A variety of fungal cell expression vectors may be used to express recombinant peptide in fungal cells. Commercially available fungal cell expression vectors which may be suitable for recombinant peptide expression include, but are not limited to, pYES2 (Invitrogen), Pichia expression vector (Invitrogen).

A variety of insect cell expression vectors may be used to express recombinant peptide in insect cells. Commercially available insect cell expression vectors which may be suitable for recombinant expression of peptide include, but are not limited to, pBlue Bac III (Invitrogen).

An expression vector containing DNA encoding the dipeptide intermediate may be used for expression of peptide in a recombinant host cell. Recombinant host cells may be prokaryotic or eukaryotic including, but not limited to, bacteria such as E. coli, fungal cells such as yeast, mammalian cells including, but not limited to, cell lines of human, bovine, porcine, monkey and rodent origin, and insect cells including, but not limited to, Drosophila and silkworm derived cell lines. Cell lines derived from mammalian species which may be suitable and which are commercially available include, but are not limited to, L cells L-M(TK-) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-KI (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The expression vector may be introduced into host cells via any one of a number of techniques including, but not limited to, transformation, transfection, lipofection, protoplast fusion, and electroporation. The expression vector-containing cells are clonally propagated and individually analyzed to determine whether they produce protein. Identification of peptide expressing host cells clones may be done by several means including, but not limited to, immunological reactivity with anti-peptide antibodies, and the presence of host cell-associated $B_1$ activity, such as peptide-specific ligand binding or signal transduction defined as a response mediated by the interaction of $B_1$-specific ligands at the receptor.

Expression of DNA may also be performed using in vitro produced synthetic mRNA or native mRNA. Synthetic mRNA or mRNA isolated from peptide producing cells can be efficiently translated in various cell-free systems including, but not limited to, wheat germ extracts and reticulocyte extracts, as well as efficiently translated in cell based systems including, but not limited to, microinjection into frog oocytes, with microinjection into frog oocytes being preferred.

To determine the DNA sequence(s) that yields optimal levels of protein, DNA molecules including, but not limited to, the following can be constructed: the full-length open reading frame of the DNA and several constructs containing portions of the DNA encoding the protein.

Levels of protein expression can be determined following the introduction, both singly and in combination, of these constructs into appropriate host cells. Following determination of the DNA cassette yielding optimal expression, for example, in transient assays, this DNA construct is transferred to a variety of expression vectors, for expression in host cells including, but not limited to, mammalian cells, insect cells, E. coli, and yeast cells such as S. cerevisiae.

Host cell transfectants and microinjected oocytes may be assayed for the level of protein by the following methods. Following an appropriate period of time to allow for expression, peptide level is measured. One method for detecting the peptide involves the direct measurement of peptide level in whole cells or cellular lysates prepared from host cells transfected with DNA.

The dipeptide alanyl-proline, Ala-Pro, is a starting material for synthesis of the ACE inhibitor, enalapril. The dipeptide Lys-Pro is a starting material for synthesis of the ACE inhibitor lysinopril. The commercially available dipeptide is currently synthesized chemically. A new bioprocess was developed which successfully eliminates the need for chemical steps to produce Ala-Pro or Lys-Pro. The process utilizes a recombinant host to overexpress a peptide containing repeats of the dipeptide Ala-Pro or Lys-Pro which is then hydrolyzed into its constituent Ala-Pro or Lys-Pro units using bacterial prolylpeptidases. Escherichia coli was chosen as the host due to the availability of expression vectors. A chemically synthesized oligonucleotide which encodes repeats of Ala-Pro and appropriate sites for ligation was cloned into the commercially available expression vector, pMAL. Fermentation of the recombinant E. coli containing the construct yielded the desired fusion product as determined by protein gels. Enzymatic processing was then employed to release Ala-Pro units. Commercially available factor X was used to release the $(Ala-Pro)_n$-20 peptide, although, the prolylpeptidases could be used as well. Prior screening for prolylpeptidases led to the identification of Lactobacillus helveticus and Xanthomonas maltophilia strains with activity against Ala-Pro-pNA and synthetic $(Ala-Pro)_n$ substrates. Crude extracts of each culture were shown to successfully process $(Ala-Pro)_n$-20 to Ala-Pro as determined by HPLC analysis. A synergistic effect was observed when extracts from both cultures were combined. The L. helveticus prolylpeptidase activity was thought to be due to exopeptidase activity as opposed to the endopeptidase activity shown by X. maltophilia. The bioprocess described has the advantage of avoiding toxic materials used in the chemical synthesis and is adaptable to other peptides.

Following expression of the dipeptide intermediate in a recombinant host cell, recombinant protein may be recovered to provide the dipeptide intermediate in purified form. Several purification procedures are available and suitable for use. As described herein, recombinant dipeptide intermediates may be purified from cell lysates and extracts by various combinations of, or individual application of salt fractionation, ion exchange chromatography, size exclusion chromatography, hydroxylapatite adsorption chromatography and hydrophobic interaction chromatography.

Following purification of the dipeptide intermediate by one or more of the techniques described herein, and those known to those skilled in the art of peptide purification, the dipeptide intermediates are further processed into the final product. In the case of the dipeptide intermediate Ala-Pro further processing into the final product known as enalapril and related compounds, is performed as described in U.S. Pat. No. 4,374,829 and U.S. Pat. No. 4,555,502, both of which are incorporated by reference herein for that purpose. In the case of the dipeptide intermediate Lys-Pro further processing into the final product known as lisinopril and related compounds, is performed as described in U.S. Pat. No. 4,374,829 and U.S. Pat. No. 4,555,502, both of which are incorporated by reference herein for that purpose.

The following Examples are provided to illustrate the present invention without, however, limiting the same thereto.

EXAMPLE 1

Construction of a Vector for Dipeptide Expression

A plasmid can be chosen for construction of a vector expressing a DNA sequence of dipeptide repeats. The vector of choice will have an origin of replication for the host in question; alternatively the vector may contain origins for expression in more than one genus to allow it to act as a shuttle vector. Antibiotic resistance genes and/or auxotrophic markers are necessary on the plasmid to verify that transformation or entry of the vector into the cell has been accomplished and to maintain vector stability by selective pressures. A strong promoter such as the tac promoter which is inducible will allow maximum expression of the downstream gene(s). A consensus ribosome binding site will be included and is specifically recognized by the preferred host. Downstream transcription termination sequences and stop codons may be included to assure the proper length of the recombinant peptide.

Alternatively, a fusion protein can be encode in the expression vector. The vector of interest will encode a truncated peptide which is generally highly expressed in the preferred host from its native promoter or another strong promoter. Cloning sites for the gene or oligonucleotide encoding a dipeptide intermediate such as an Ala-Pro or Lys-Pro repeat can be designed by synthetic techniques or may be in place based on the 5' or 3' DNA sequences of the repeats. The resulting DNA construct when expressed gives a protein containing the truncated enzyme or binding protein such as the maltose binding protein from E. coli fused to the dipeptide intermediate sequence. Separation can be accomplished easily making use of the fusion partner, and subsequent processing will remove the 5' peptide. In some hosts, signal or leader peptides to allow proper extracellular transport may be used to secrete the desired product.

Codon preferences in the host organism can be manipulated to enhance expression. The codon usage will generally be biased in the host cell such that one or more codons are used predominantly during expression of specific genes. Strongly expressed genes giving higher levels of proteins or peptides typically are encoded by codons which are favored or used more frequently than others. In E. coli, two codons are available for lysine, AAA and AAG; four codons are possible for proline, CCA, CCC, CCG, and CCU. The codon sequence CCG is a more frequently used codon and thus Pro residues in the synthetic Lys-Pro oligonucleotide would be designed as CCG. Lys is encoded by only two codons with no clear preference and thus both AAA and AAG would be chosen when designing the oligonucleotide which becomes the Lys-Pro repeat expressed as a Lys-Pro polypeptide. For an Ala-Pro oligonucleotide, GCT and GCA are preferred codon sequences and would thus be chosen for maximum expression in E. coli.

EXAMPLE 2

Cloning of the DNA into E. coli Expression Vectors

Recombinant peptide is produced in E. coli following the transfer of the peptide expression cassette into E. coli expression vectors including, but not limited to, the pET series (Novagen). The pET vectors place peptide expression under control of the tightly regulated bacteriophage T7 promoter. Following transfer of this construct into an E. coli host which contains a chromosomal copy of the T7 RNA polymerase gene driven by the inducible lac promoter, expression of peptide is induced when an appropriate lac substrate (IPTG) is added to the culture. The levels of expressed peptide are determined by the assays described herein.

The cDNA encoding the entire open reading frame for the peptide is inserted into the NdeI site of pET 11a. Constructs in the positive orientation are identified by sequence analysis and used to transform the expression host strain BL21. Transformants are then used to inoculate cultures for the production of protein. Cultures may be grown in M9 or ZB media, whose formulation is known to those skilled in the art. After growth to an $OB_{600}$=1.5, expression of peptide is induced with 1 mM IPTG for 3 hours at 37° C.

EXAMPLE 3

Cloning of DNA into a Vectors for Expression in Insect Cells

Baculovirus vectors, which are derived from the genome of the AcNPV virus, are designed to provide high level expression of cDNA in the Sf9 line of insect cells (ATCC CRL# 1711). Recombination baculoviruses expressing DNA encoding dipeptide intermediate is produced by the following standard methods (InVitrogen Maxbac Manual): the DNA constructs are ligated into the polyhedrin gene in a variety of baculovirus transfer vectors, including the pAC360 and the BlueBac vector (InVitrogen). Recombinant baculoviruses are generated by homologous recombination following co-transfection of the baculovirus transfer vector and linearized AcNPV genomic DNA [Kitts, P. A., Nuc. Acid. Res. 18, 5667 (1990)] into Sf9 cells. Recombinant pAC360 viruses are identified by the absence of inclusion bodies in infected cells and recombinant pBlueBac viruses are identified on the basis of β-galactosidase expression (Summers, M. D. and Smith, G. E., Texas Agriculture Exp. Station Bulletin No. 1555). Following plaque purification, peptide expression is measured by the assays described herein.

The cDNA encoding the entire open reading frame for peptide is inserted into the BamHI site of the pBlueBacII. Constructs in the positive orientation are identified by sequence analysis and used to transfect Sf9 cells in the presence of linear AcNPV wild type DNA.

Authentic peptide is found in association with the infected cells. Peptide is extracted from infected cells by hypotonic or detergent lysis.

Alternatively, the peptide is expressed in the Drosophila Schneider 2 cell line by cotransfection of the Schneider 2 cells with a vector containing the peptide DNA downstream and under control of an inducible metallothionin promoter, and a vector encoding the G418 resistant neomycin gene. Following growth in the presence of G418, resistant cells are obtained and induced to express the peptide by the addition of $CuSO_4$.

EXAMPLE 4

Cloning of DNA into a Yeast Expression Vector

Recombinant peptide is produced in the yeast S. cerevisiace following the insertion of the optimal DNA cistron into expression vectors designed to direct the intracellular or extracellular expression of heterologous proteins. In the case of intracellular expression, vectors such as EmBLyex4 or the like are ligated to the cistron [Rinas, U. et al., Biotechnology 8, 543–545 (1900); Horowitz B. et al., *J. Biol. Chem.* 265, 4189–4192 (1989)]. For extracellular expression, the cistron is ligated into yeast expression vectors which fuse a secretion signal. The levels of expressed peptide are determined by the assays described herein.

EXAMPLE 5

Purification of Recombinant Peptide

Recombinantly produced peptide may be purified by antibody affinity chromatography.

Peptide antibody affinity columns are made by adding the anti-peptide antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) together with appropriate membrane solubilizing agents such as detergents and the cell culture supernatants or cell extracts containing solubilized peptide are slowly passed through the column. The column is then washed with phosphate-buffered saline together with detergents until the optical density (A280 falls to background, then the protein is eluted with 0.23M glycine-HCl (pH 2.6) together with detergents. The purified protein is then dialyzed against phosphate buffered saline.

EXAMPLE 6

Recombinant Productions of Ala-Pro Dipeptide

Ala-Pro Expression.

The strategy for production of an Ala-Pro polypeptide in *E. coli* involved the cloning of a sequence encoding repeats of Ala-Pro. A number of commercially available systems are available. To minimize development time, a commercially available expression system, p-MAL, was purchased from New England Biolabs. The system makes use of a vector containing a gene for the maltose binding protein adjacent to a polylinker site into which DNA sequence of interest such as an Ala-Pro repeat codon can be cloned. Following induction of a clone containing the above vector, a fusion protein (maltose-Ala-Pro$_n$) would be expressed, the maltose binding domain used to bind a maltose column, and the maltose domain cleaved by factor X following isolation.

Toward that end, two complementary oligonucleotides were designed (87 mer and 91 mer) to code for 14 Ala-Pro units and a stop codon. The oligos were synthesized by Standard methods. The oligos were purified by SDS-PAGE and extracted from the gel. A directional cloning strategy, using a blunt end and a cohesive end, was used to assure proper alignment and ligation of the ala-pro gene into the plasmid. Clones were selected following transformation of *E. coli*. Protein analysis and induction experiments on one clone, AP/2, showed that fusion proteins were being produced following induction. Sizing of bands on SDS-PAGE gels suggests more than one fusion product. Nevertheless the induction and production of the fusion protein is clear.

Concerns about rearrangement of the cloned sequence and proper recognition of the stop codon designed into the oligonucleotide led to sequencing of the inserted DNA. DNA from the clone was sequenced using the M13 universal primer. Interestingly, the sequence of the insert codes for 20 ALA-PRO repeats instead of the 14 Ala-Pro repeats. The stop codon TAG is present at the end of the 20 repeats. The presence of (Ala-Pro)$_{20}$ is thought to be due to the two oligonucleotides having annealed in a staggered pattern, and the resulting gaps were filled by the polymerase during recombination. The annealing is not unusual due to the highly repeated sequence. In this case, it may be beneficial as it resulted in a longer gene (and thus more Ala-Pro repeats).

Hydrolysis of Ala-Pro Substrates.

Three bacterial cultures, *Lactobacillus helveticus*, L. sp., and *Xanthomonas maltophilia*, reported in the literature to produce prolyldipeptidase activity were obtained from the ATCC. The cultures were grown in 250 ml flasks and examined for hydrolytic activity against a commercially available colorimetric substrate, Ala-Pro-pNA (source). All three cultures provided activity of which the majority was cell associated (Table 1). Culture stocks were subsequently made on slants and in frozen FVM's. For optimal growth, the lactobacilli required a microaerophilic chamber for slants and stationary liquid culture in flasks.

TABLE 1

Specific Activity of Prolyldipeptidases on (ALA-PRO)2

| Culture[4] | Sp. Act (U/mg)[1] | U/L[1] | pH Opt.[2] | Temp. Opt.[3] |
|---|---|---|---|---|
| L. Helveticus | .156 | 8 | 5.6 | 50° C. |
| L. unk. sp. | .085 | 14.7 | 6.0 | 40° C. |
| X. maltophilia | .446 | 107 | 6.6 | 45° C. |

[1]Where U- μmol ALA-PRO released/min at 37° C. and optimum pH
[2]Citrate phosphate buffer at optimum temperature
[3]Carried out at pH 8.0
[4]Enzyme extracts from virtis homogenized cells It was desirable to obtain substrates which might reflect the actual oligomeric Ala-Pro substrate which would be available following growth of a recombinant *E. coli*. In that regard, peptide oligomers for use as prolylpeptidase substrates were synthesized by Biosynthesis Inc. An HPLC method to separate low molecular weight peptides and free amino acids was developed to evaluate enzyme activity against authentic Ala-Pro substrates. The peptides from Biosynthesis were subsequently purified using the HPLC method. Following collection of fractions from HPLC, Ala-Pro peptides of 2, 4, and 6 repeats were available. The peptides temperature and pH optima have been determined for each of the crude extracts (Table 2). *L. helveticus* provided the highest enzyme titer and specific activities. Recommended complex media from the literature were used for all studies, no medium optimization or screening was done. Based on differences in the appearance of hydrolytic products, it appears that the lactobacilli produce an endo-prolyldipeptidase and the Xanthomonas produces an exopeptidase. A benefit of this observation is shown by combining enzymes to achieve a synergistic effect in hydrolysis of Ala-Pro6.

| Enzyme source | Protein (mg/ml) | U/Liter[1] (A-P)$_2$ | Specific Activity (U/mg)[1] | | |
|---|---|---|---|---|---|
| | | | (A-P)$_2$ | (A-P)$_4$ | (A-P)$_6$ |
| Lactobacillus helveticus | 2.04 | 186 | 1.82 | 2.15 | 0.94 |
| Lactobacillus unk. species | 3.02 | 156 | 1.53 | 1.53 | 0.87 |

-continued

| Enzyme source | Protein (mg/ml) | U/Liter[1] (A-P)$_2$ | Specific Activity (U/mg)[1] | | |
|---|---|---|---|---|---|
| | | | (A-P)$_2$ | (A-P)$_4$ | (A-P)$_6$ |
| Xanthomonas maltophilia | 0.70 | 28 | 0.17 | 0.35 | 0.43 |

[1]Units defined as mmol ALA-PRO release per minute at 35° C. and pH 7.0.
[2]Enzyme extracts from "bead beater" homogenized cells.

It was found that when an excess of enzyme (600×concentrated as compared to normal assay conditions) was introduced to Ala-Pro, the Ala-Pro substrate was hydrolyzed to alanine and proline. Metallo-and cysteine proteases inhibitors were effective in inhibiting Ala-Pro hydrolysis while having little effect on hydrolysis of Ala-Pro$_6$ to Ala-Pro suggesting that a separate enzyme facilitates the Ala-Pro cleavage. Partial purification should also remove undesirable activities from these crude extracts.

In the case of the dipeptide intermediate Ala-Pro further processing into the final product known as enalapril and related compounds, is performed as described in U.S. Pat. No. 4,374,829 and U.S. Pat. No. 4,555,502, both of which are incorporated by reference herein for that purpose.

EXAMPLE 7

Recombinant Production of Lys-Pro Dipeptide from a Recombinant Plant Protein Naturally occurring sequences rich in Lys-Pro encoding sequences can be found in the cell wall protein gene family of soybeans (*Glycine max*) [From: Hong et al., *J. Biol. Chem.*, 1990]. The three proline-rich protein genes of soybean are SbPRP1, SbPRP2, and SbPRP3 which are 256, 230, and 90 amino acids in length, respectively. The amino acid compositions for these proteins indicate that 34 to 40% of the residues are proline and 18 to 25% are lysine. Of particular interest, SbPRP1 contains 37 Lys-Pro amino acid pairs in the peptide sequence and thus is an excellent source of Lys-Pro dipeptide. SbPRP3 encodes 12 Lys-Pro dipeptide sequences including two Lys-Pro-Lys-Pro (SEQ ID NO:1) repeat sequences encoded at 183 and 195 bp in the gene.

Cloning of the Lys-Pro rich SbPRP1 gene is accomplished by generating PCR primers based on the reported DNA sequences. DNA fragments containing the sequences of interest are generated using the primers and a library containing the soybean DNA. The resulting DNA rich in Lys-Pro codons, is ligated to appropriate restriction sites in an expression vector. Using an *E. coli* host, the soybean peptides are expressed and recovered from the lysed cells. Using *Lactobacillus helveticus* or the prolylpeptidase derived from this strain, the protein is hydrolyzed into constituent amino acids and small peptides including the Lys-Pro residues. Chromatography or extraction will provide relatively pure Lys-Pro.

An alternative method is to synthesize oligonucleotides corresponding to the Lys-Pro-Lys-Pro (SEQ ID NO:1) repeats in SbPRP3 [or use two sets back to back but not contiguous in the natural sequence] designed with the appropriate restriction sites for insertion into the expression vector of interest. Expression in the proper host gives significant quantities of Lys-Pro as oligopeptides. Using *Lactobacillus helveticus* or the prolylpeptidase derived from this strain, the lysine and proline rich peptide is hydrolyzed into Lys-Pro residues. Alternatively, a proline specific peptidase from *Flavobacterium menigosepticum* [Yoshimoto, T. et al., *Agric. Biol. Chem.*, 42:2417, 1978] is used to hydrolyze the peptide. Chromatography or extraction provide relatively pure Lys-Pro.

In the case of the dipeptide intermediate Lys-Pro further processing into the final product known as lysinopril and related compounds, is performed as described in U.S. Pat. No. 4,374,829 and U.S. Pat. No. 4,555,502, both of which are incorporated by reference herein for that purpose.

EXAMPLE 8

Recombinant Production of Ala-Pro Dipeptide from or Recombinant Amphibian Protein An acidic polypeptide of approximately 75 kDa found in storage granules in skin glands of *Xenopus laevis* referred to as the APEG protein is rich in Ala-Pro dipeptides [Gmachl, M. et al., *FEBS Letters*, 260:145–148]. At least 80% of the mass is alanine, proline, glutamic acid, and glycine at a ratio of 2:2:1:1.

A cDNA expression library in a lambda derived vector can be screened with oligonucleotide probes from the published sequence to isolate the fragment of interest. Alternatively, antibodies to the APEG can be used to screen such a cDNA expression library. The fragment of interest can be isolated from the clone of interest and inserted into an expression vector. (Processing of the resulting peptide as per Example 6—Hydrolysis of Ala-Pro Substrates).

A preferred method is to synthesize an oligonucleotide corresponding to the natural APEG DNA sequences for Ala-Pro-Ala-Pro-Ala-Pro (SEQ ID NO:2) (5'-CACCAGCTCCAGCACCAG-3';SEQ ID NO:3). With the appropriate restriction sites in the oligonucleotide, the DNA is cloned into an expression vector for expression in a recombinant host cell as set forth above. The polypeptide containing the dipeptide intermediate repeats is hydrolyzed enzymatically as described above, and the dipeptide intermediate Ala-Pro is isolated for further processing into the product.

In the case of the dipeptide intermediate Ala-Pro further processing into the final product known as enalapril and related compounds, is performed as described in U.S. Pat. No. 4,374,829 and U.S. Pat. No. 4,555,502, both of which are incorporated by reference herein for that purpose.

---

What is claimed is:

1. A process for producing an Ala-Pro dipeptide, which comprises:
   (a) transfecting a DNA expression vector into suitable host cells wherein said DNA expression vector comprises a DNA molecule which encodes an oligopeptide or polypeptide containing multiple direct repeats of said Ala-Pro dipeptide;
   (b) culturing said host cells under conditions suitable for expression of said oligopeptide or polypeptide from said DNA expression vector;
   (c) cleaving said expressed oligopeptide or polypeptide with an enzyme capable of cleaving said Ala-Pro dipeptides from each other, thereby releasing said Ala-Pro dipeptides, wherein said enzyme is selected as a combination of at least an exo- and an endopeptidase selected from the group consisting of: factor X, Lactobacillus sp. prolypeptidase, *Lactobacillus helveticus* prolypeptidase, *Flavobacterium meningosepticum* prolypeptidase, and *Xanthomonas maltophilia* prolypeptidase; and,
   (d) isolating and purifying said Ala-Pro dipeptides.

2. The process of claim 1 wherein said oligopeptide or polypeptide contains from about 14 to 20 direct repeats of Ala-Pro.

3. The process of claim 1 wherein said DNA expression vector expresses the oligopeptide as set forth in SEQ ID NO:2.

4. The process of claim 1 wherein said DNA expression vector encodes a fusion protein comprising a cleavable fragment linked to said oligopeptide or polypeptide containing multiple direct repeats of said Ala-Pro dipeptide.

5. The process of claim 4 wherein said cleavable fragment is the maltose binding protein.

6. The process of claim 4 wherein said oligopeptide or polypeptide contains from about 14 to 20 direct repeats of Ala-Pro.

7. The process of claim 4 wherein said DNA expression vector expresses the oligopeptide as set forth in SEQ ID NO:2.

8. The process of claim 5 wherein said oligopeptide or polypeptide contains from about 14 to 20 direct repeats of Ala-Pro.

9. The process of claim 5 wherein said DNA expression vector expresses a product comprising the oligopeptide as set forth in SEQ ID NO:2.

10. A process for producing a Lys-Pro dipeptide, which comprises:
   (e) transfecting a DNA expression vector into suitable host cells wherein said DNA expression vector comprises a DNA molecule which encodes an oligopeptide or polypeptide containing multiple direct repeats of said Lys-Pro dipeptide;

(f) culturing said host cells under conditions suitable for expression of said oligopeptide or polypeptide from said DNA expression vector;

(g) cleaving said expressed oligopeptide or polypeptide with an enzyme capable of cleaving said Lys-Pro dipeptides from each other, thereby releasing said Lys-Pro dipeptides, wherein said enzyme is selected as a combination of at least an exo- and an endopeptidase selected from the group consisting of: factor X, Lactobacillus sp. prolypeptidase, *Lactobacillus helveticus* prolypeptidase, *Flavobacterium meningosepticum* prolypeptidase, and *Xanthomonas maltophilia* prolypeptidase; and, (h) isolating and purifying said Lys-Pro dipeptides.

11. The process of claim 10 wherein said DNA expression vector expresses the oligopeptide as set forth in SEQ ID NO:1.

12. The process of claim 10 wherein said DNA expression vector encodes a fusion protein comprising a cleavable fragment linked to said oligopeptide or polypeptide containing multiple direct repeats of said Lys-Pro dipeptide.

13. The process of claim 12 wherein said DNA expression vector expresses a product comprising the oligopeptide as set forth in SEQ ID NO:1.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
       (A) LENGTH: 4 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:1:

Lys Pro Lys Pro
1

(2) INFORMATION FOR SEQ ID NO:2:

(i) SEQUENCE CHARACTERISTICS:
       (A) LENGTH: 6 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:2:

Ala Pro Ala Pro Ala Pro
1               5

(2) INFORMATION FOR SEQ ID NO:3:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "oligonucleotide"

(xi) SEQUENCE DESCRIPTION: SEQ ID NO:3:

CACCAGCTCC AGCACCAG                                        18